US012758802B2

(12) United States Patent
Choi

(10) Patent No.: US 12,758,802 B2
(45) Date of Patent: Oct. 13, 2026

(54) CARTRIDGE FOR MOVING ULTRASOUND FOCAL POINT AND ULTRASOUND TREATMENT DEVICE COMPRISING SAME

(71) Applicant: Jun Young Choi, Namyangju-si (KR)

(72) Inventor: Jun Young Choi, Namyangju-si (KR)

(73) Assignee: JION MEDITECH CO. LTD., Anyang-si (KR)

( * ) Notice: Subject to any disclaimer, the term of this patent is extended or adjusted under 35 U.S.C. 154(b) by 195 days.

(21) Appl. No.: 18/725,269

(22) PCT Filed: Dec. 20, 2022

(86) PCT No.: PCT/KR2022/020771
§ 371 (c)(1),
(2) Date: Jun. 28, 2024

(87) PCT Pub. No.: WO2023/128441
PCT Pub. Date: Jul. 6, 2023

(65) Prior Publication Data

US 2025/0058151 A1 Feb. 20, 2025

(30) Foreign Application Priority Data

Dec. 28, 2021 (KR) ........................ 10-2021-0190435
Jan. 17, 2022 (KR) ........................ 10-2022-0006355

(51) Int. Cl.
*A61N 7/02* (2006.01)
*A61N 7/00* (2006.01)

(52) U.S. Cl.
CPC ................. *A61N 7/02* (2013.01); *A61N 7/00* (2013.01); *A61N 2007/0034* (2013.01); *A61N 2007/0082* (2013.01); *A61N 2007/0091* (2013.01)

(58) Field of Classification Search
CPC .... A61N 7/02; A61N 7/00; A61N 2007/0034; A61N 2007/0082; A61N 2007/0091; A61B 8/4461
See application file for complete search history.

(56) References Cited

U.S. PATENT DOCUMENTS

2019/0366129 A1* 12/2019 Park ......................... A61N 7/02
2021/0387023 A1* 12/2021 Kim ......................... A61N 7/02

FOREIGN PATENT DOCUMENTS

CN 105433984 A * 3/2016 ........... A61B 8/4461
KR 20120040909 A 4/2012

(Continued)

OTHER PUBLICATIONS

International Search Report—PCT/KR2022/020771 dated Apr. 14, 2023.

*Primary Examiner* — Sean D Mattson
(74) *Attorney, Agent, or Firm* — CANTOR COLBURN LLP

(57) ABSTRACT

Provided is a cartridge for moving an ultrasound focal point. The cartridge for moving an ultrasound focal point includes: a drive gear rotatably installed around a first axis; a driven gear configured to rotate around a second axis parallel to the first axis and move horizontally along the second axis at the same time by rotation power received from the drive gear; and an ultrasound irradiation moving body that is horizontally moved with the driven gear and vertically moved in a direction perpendicular to the first axis or the second axis. Thus, the ultrasound focal point can be stably moved in the horizontal and vertical directions, and thus the treatment efficiency can be improved.

7 Claims, 7 Drawing Sheets

(56) References Cited

FOREIGN PATENT DOCUMENTS

| | | | | | |
|---|---|---|---|---|---|
| KR | 101335476 B1 | | 12/2013 | | |
| KR | 101429002 B1 | | 8/2014 | | |
| KR | 101700334 B1 | * | 1/2017 | ............... | A61B 8/44 |
| KR | 101756618 B1 | * | 7/2017 | ............... | A61N 7/02 |
| KR | 101893584 B1 | | 8/2018 | | |
| KR | 102256560 B1 | * | 5/2021 | ............... | B06B 1/00 |

* cited by examiner

CARTRIDGE FOR MOVING ULTRASOUND FOCAL POINT AND ULTRASOUND TREATMENT DEVICE COMPRISING SAME

TECHNICAL FIELD

The present invention relates to an ultrasound focal point moving cartridge, and more specifically, to an ultrasound focal point moving cartridge which enables the movement of a ultrasound focal point in an ultrasound treatment device used for skin care.

BACKGROUND ART

As interest in appearance increases, the market for skin care devices is growing. In particular, since invasive methods are less safe and have high patient aversion, non-invasive methods are gaining popularity. Among the non-invasive methods, skin care devices using high intensity focused ultrasound (HIFU) are being developed. The skin care devices using high intensity focused ultrasound (HIFU) focus high-intensity ultrasound on a point within human skin, causing thermal damage to the focused area. The thermal damage can lead to the composite action of new collagen fibers in the skin, thereby improving skin elasticity or reducing wrinkles. The skin care devices using high intensity focused ultrasound are known to be safe for the skin and provide significant skin improvement effects.

Meanwhile, the skin layers sequentially include the epidermis, the dermis, the subcutaneous fat layer, and the superficial muscular aponeurotic system (SMAS) layer. To obtain effective skin improvement, the focused ultrasound must be evenly irradiated to the skin layers. In addition, focused ultrasound must be applied evenly across the entire surface of the skin to achieve uniform skin improvement effects.

However, there were inconveniences in that an operator had to manipulate the device to move the depth of the ultrasound focal point or directly move the ultrasound treatment device along the skin surface to evenly apply the focused ultrasound.

Furthermore, even if the ultrasound focal point automatically moves horizontally and/or vertically based on the user's skin surface, the mechanical structure of the device for such movement is unstable, causing vibration and noise, and leading to decreased durability of the device.

Meanwhile, the aforementioned conventional art is technical information held by the inventor or acquired during the process of inducing the present disclosure, and cannot necessarily be considered known art publicly disclosed to the general public before the filing of the present disclosure.

DISCLOSURE

Technical Problem

Accordingly, the present invention has been made in view of the above-mentioned problems occurring in the related art, and it is an object of the present invention to provide an ultrasound focal point moving cartridge which enables the stable movement of a ultrasound focal point in the horizontal direction and in the vertical direction, thereby improving the efficiency of the treatment.

Technical Solution

To accomplish the above-mentioned objects, according to the present invention, there is provided an ultrasound focal point moving cartridge including: a drive gear rotatably installed around a first axis; a driven gear configured to rotate around a second axis parallel to the first axis and move horizontally along the second axis by rotation power received from the drive gear; and an ultrasound irradiation moving body which is horizontally moved with the driven gear and vertically moved in a direction perpendicular to the first axis or the second axis.

The driven gear moves along a lead screw which is fixedly installed along the second axis.

The driven gear includes a cam part eccentric to the second axis, and the ultrasound radiation moving body includes a push rod which is in contact with the cam part.

The driven gear and the ultrasound radiation moving body respectively include a groove and a protrusion corresponding to each other, or a protrusion and a groove, for the horizontal movement of the ultrasound radiation moving body.

The ultrasound focal point moving cartridge further includes a carriage, and the carriage is installed not to be moved vertically, and guides the horizontal movement and the vertical movement of the ultrasound radiation moving body.

Between the ultrasound radiation moving body and the carriage, an elastic means which supplies elastic force so that the ultrasound radiation moving body is pressed against the cam part of the driven gear is provided.

The ultrasound treatment device according to an embodiment of the present invention includes the ultrasound focal point moving cartridge.

Advantageous Effect

According to an embodiment of the present invention, the ultrasound focal point can be moved in the horizontal direction and in the vertical direction, thereby improving the efficiency of the treatment.

Furthermore, during the operation of the ultrasound treatment device, the movement of the ultrasound focal point in horizontal and vertical directions can effectively reduce vibration and noise and enhance the durability of the device.

Other effects that may be obtained or anticipated from the embodiments of the present invention will be directly or implicitly disclosed in the detailed description of the embodiments. That is, various effects anticipated according to the embodiments of the present invention will be disclosed in the detailed description below.

MODE FOR INVENTION

Figure 1:
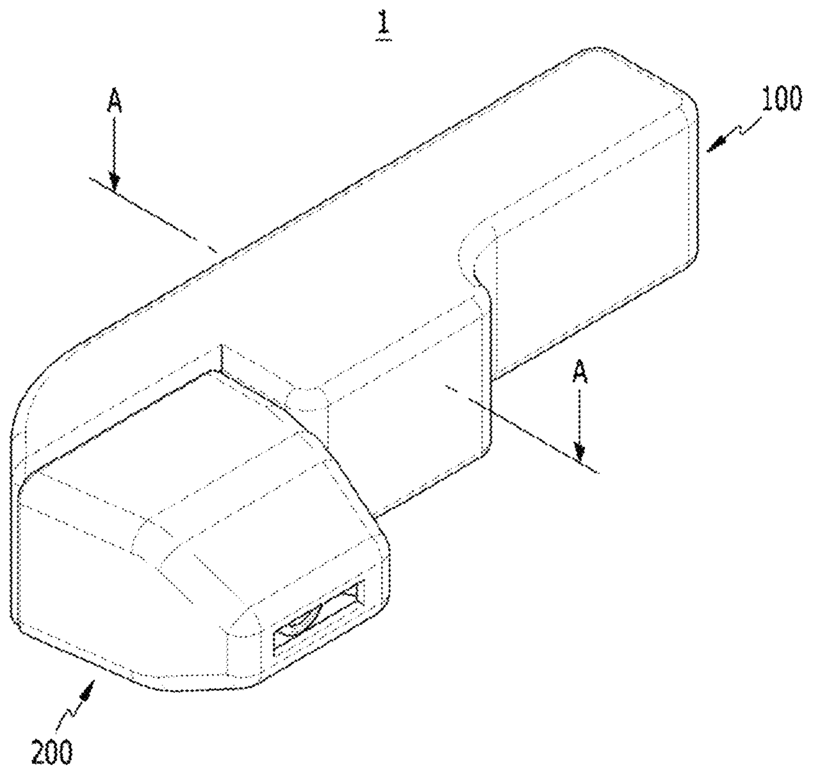
FIG. 1 is a perspective view of an ultrasound treatment device according to an embodiment of the present invention.

Hereinafter, preferred embodiments of the present invention will be described in detail with reference to the accompanying drawings.

Moreover, it should be understood that the embodiments and configurations illustrated in the drawings are merely exemplary embodiments of the present invention and do not represent all the technical ideas of the present invention. For this reason, it should be understood that there are various equivalents and modifications that can replace the configurations at the time of application.

To clearly describe the present invention, parts unrelated to the description have been omitted, and the same reference numerals are used throughout the specification for the same or similar components.

The size and thickness of each component illustrated in the drawings may be arbitrarily expressed for the convenience and clarity of the description, and the present invention is not necessarily limited to what is illustrated in the drawings.

In the entire specification of the present disclosure, when any portion "includes" any component, this does not exclude other components but means that any other component can be further included, unless specifically stated otherwise.

Furthermore, terms such as " . . . unit", " . . . means", " . . . part", " . . . member", " . . . module" in the specification denote units that perform at least one function or operation.

Moreover, terms like "horizontal" or similar terms in the specification mean a direction approximately horizontal to a user's skin surface when the ultrasound treatment device according to the present invention is used, and terms like "vertical" or similar terms mean a direction approximately perpendicular to the user's skin surface.

Hereinafter, the ultrasound treatment device according to an embodiment of the present invention will be described with reference to FIGS. 1 and 2.

Figure 2:
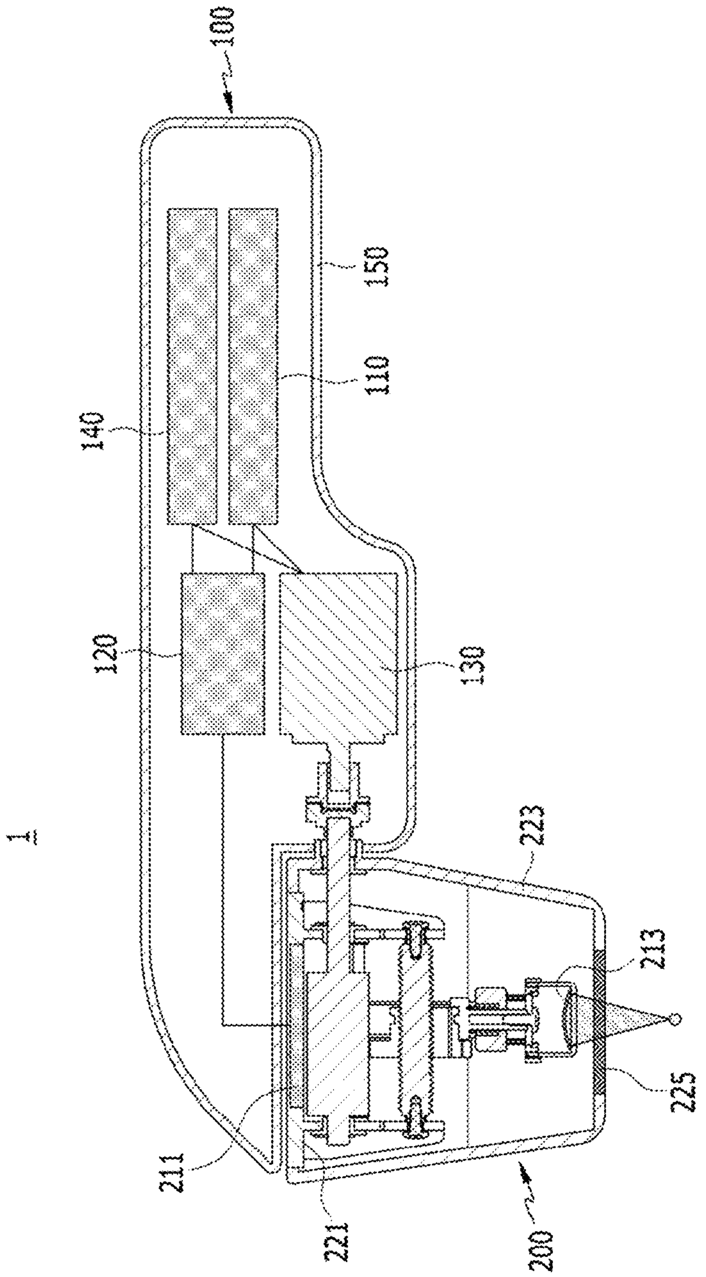
FIG. 2 is a cross-sectional view taken along line A-A of FIG. 1.

FIG. 1 is a perspective view of an ultrasound treatment device according to an embodiment of the present invention, and FIG. 2 is a cross-sectional view taken along line A-A of FIG. 1.

The ultrasound treatment device 1 according to an embodiment of the present invention may include a handpiece 100 and an ultrasound focal point moving cartridge 200.

The handpiece 100 may include a controller 110, a power amplifier 120, a motor 130, a battery 140, and a handpiece housing 150.

The controller 110 transmits operational commands from a power switch (not shown) to the power amplifier 120. The power amplifier 120 outputs high frequency to the cartridge board 210, which can generate high-frequency ultrasound for driving an ultrasound transducer. The generated high frequency can be converted into ultrasound by the cartridge board 211 and the ultrasound transducer 213 and then emitted.

The motor 130 generates driving force. The driving force is transmitted to the ultrasound focal point moving cartridge 200 and is used for moving the ultrasound focal point.

The power required for the power amplifier 120 and the motor 130 can be supplied by the battery 140. The controller 110, the power amplifier 120, the motor 130, and the battery 140 can be placed within the handpiece housing 150.

Meanwhile, the ultrasound focal point moving cartridge 200 may include a cartridge bracket 221, a cartridge housing 223, and a film part 225. The cartridge bracket 221 may be equipped with mechanisms for the horizontal movement and the vertical movement of the ultrasound focal point, and the mechanisms can be placed within the cartridge housing 223. The cartridge housing 223 may be provided with the film part 225 for the emission of ultrasound. The ultrasound can be emitted through the film part 225 from the ultrasound focal point moving cartridge to be used for skin care.

Hereinafter, with reference to FIGS. 3 to 6, the ultrasound focal point moving cartridge according to an embodiment of the present invention will be described.

Figure 3:
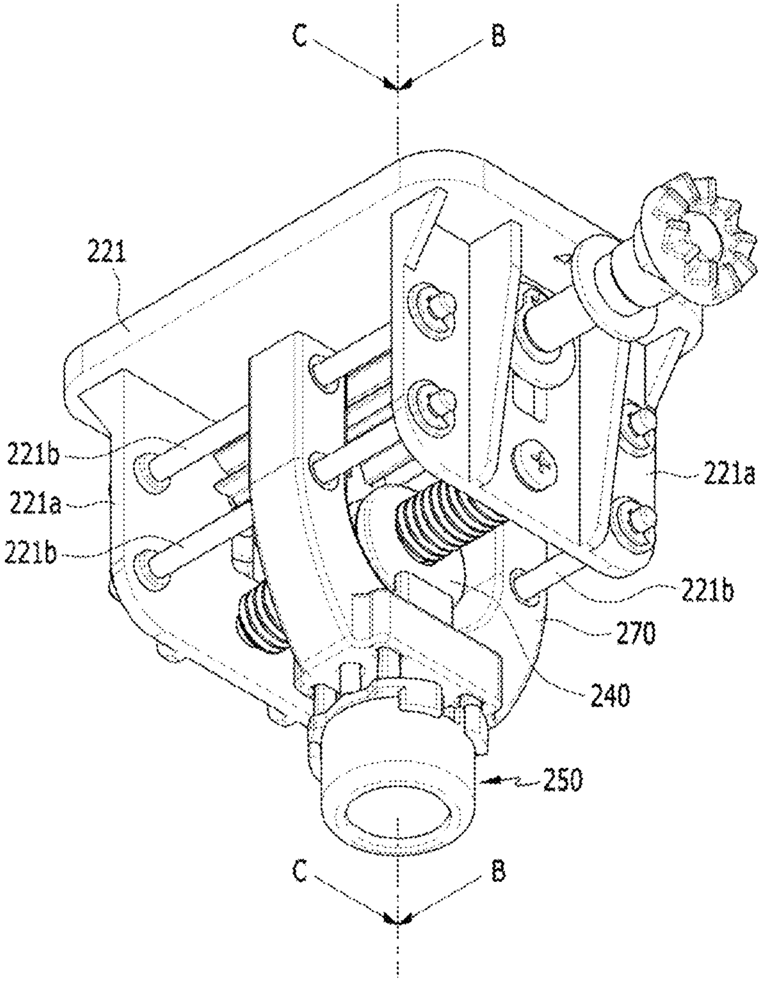
FIG. 3 is a perspective view of an ultrasound focal point moving cartridge according to an embodiment of the present invention.
Figure 4:
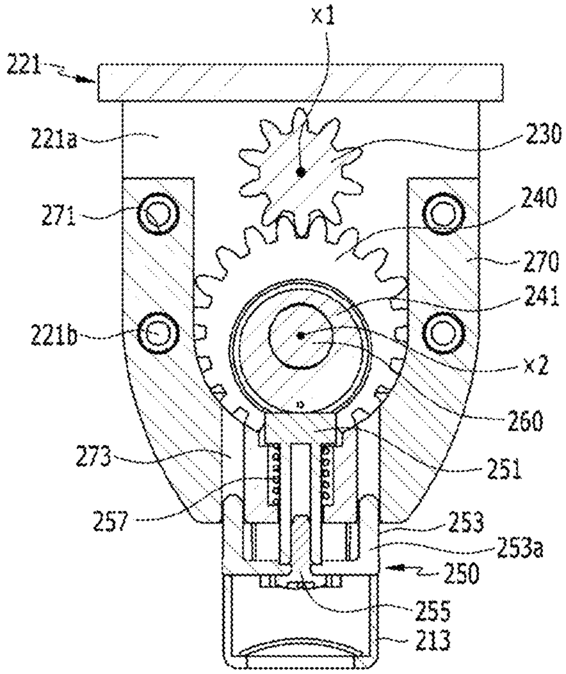
FIG. 4 is a cross-sectional view taken along line B-B of FIG. 3.
Figure 5:
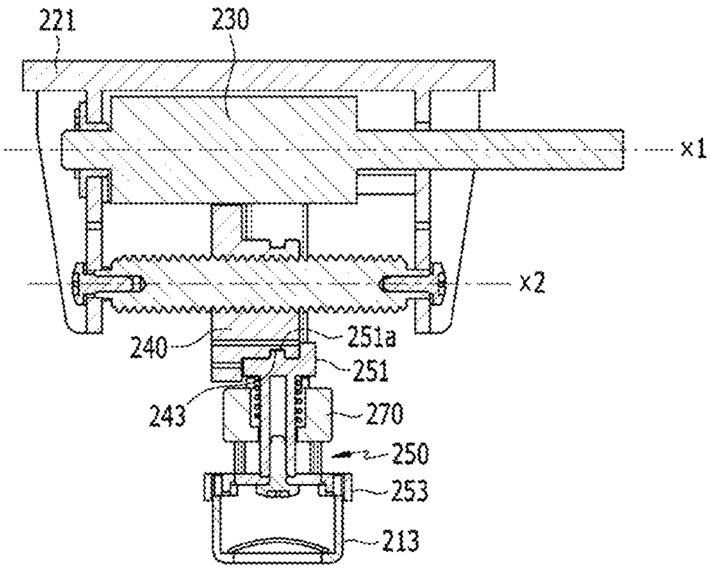
FIG. 5 is a cross-sectional view taken along line C-C of FIG. 3.
Figure 6:
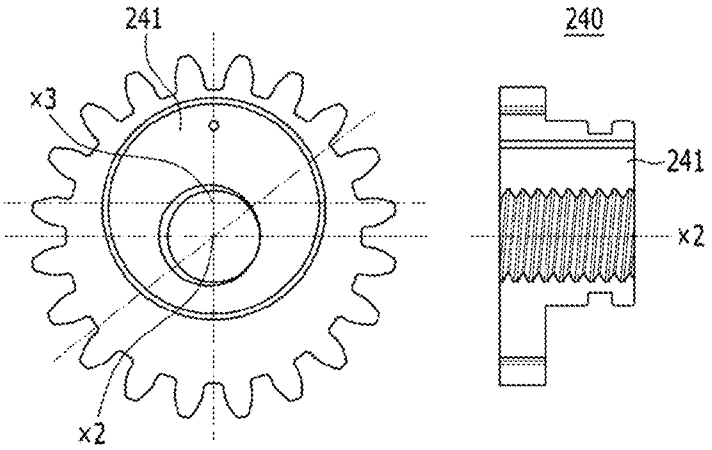
FIG. 6 is a view illustrating a driven gear according to an embodiment of the present invention.

FIG. 3 is a perspective view of an ultrasound focal point moving cartridge according to an embodiment of the present invention, FIG. 4 is a cross-sectional view taken along line B-B of FIG. 3, FIG. 5 is a cross-sectional view taken along line C-C of FIG. 3, and FIG. 6 is a view illustrating a driven gear according to an embodiment of the present invention.

The ultrasound focal point moving cartridge 200 according to an embodiment of the present invention may include a drive gear 230, a driven gear 240, and an ultrasound radiation moving body 250.

The drive gear 230 can be rotatably installed around a first hypothetical axis X1. In one aspect, the cartridge bracket 221 may have two wall parts 221*a*, and the drive gear 230 can be rotatably installed on the two wall parts 221*a* of the cartridge bracket 221. The drive gear 230 can be rotated by receiving driving force from the motor 130.

The driven gear 240 receives rotational force from the drive gear 230 and can rotate around a second hypothetical axis X2 and can move horizontally along the second axis X2. The second axis X2 can be a horizontal axis relative to the first axis X1.

According to an embodiment of the present invention, the driven gear 240 can move horizontally along a lead screw 260 fixed along the second axis X2. The lead screw 260 can be installed between the two wall parts 221*a* of the cartridge bracket 221, and can be fixed in place non-rotatably.

In one aspect, the inner diameter of the driven gear 230 may be provided with a thread corresponding to a thread on the outer diameter of the lead screw 260. Accordingly, the driven gear 240 can rotate and move horizontally along the lead screw 260.

The ultrasound radiation moving body 250 can move horizontally with the driven gear 250 and can move vertically in a direction perpendicular to either the first axis X1 or the second axis X2.

In one aspect, the ultrasound radiation moving body 250 may include a push rod 251, and an ultrasound transducer holder 253. The push rod 251 and the ultrasound transducer holder 253 can be coupled by a fixing bolt 255. By providing the push rod 251 and the ultrasound transducer holder 253 as separate parts, a carriage 270 can be interposed between the push rod 251 and the ultrasound transducer holder 253. In other words, the carriage 270 can be interposed between the push rod 251 and the ultrasound transducer holder 253, and then, the push rod 251 and the ultrasound transducer holder 253 are assembled. Therefore, the assembly of the push rod 251, the ultrasound transducer holder 253, and the carriage 270 can be improved.

Meanwhile, the ultrasound transducer holder 253 may be coupled with an ultrasound transducer 213.

According to an embodiment of the present invention, the driven gear 240 may include a cam part 241 eccentric to a second axis X2.

Referring to FIG. 6, a cam part 241 may be provided on one side of the driven gear 240, and the cam part 241 may be eccentric to the second axis X2, which is a rotational axis of the driven gear 240. In one aspect, the cam part 241 is formed in a circular shape about a third axis X3, and may rotate around the second axis X2, not the third axis X3.

As illustrated in FIG. 6, the shape of the cam part 241 viewed from the direction of the second axis X2 may be circular, but is not limited thereto. The cam part 241 can also be provided in an oval, polygonal, or other shapes. When the driven gear 240 rotates around the second axis X2, the cam part 241 also rotates around the second axis X2. Referring to FIG. 5, the cam part 241 of the ultrasound focal point moving cartridge 200 according to the present invention can be designed with relatively small width, and the volume and mass of the cam part 241 can also be designed to be relatively small. Accordingly, compared to a cam part with large volume and mass, the eccentrically rotating cam part 241 can effectively reduce vibration and noise generated during operation, and improve the durability of the device.

The ultrasound radiation moving body 250 may include a push rod 251 that is in contact with the cam part 241 of the driven gear 240.

The push rod 251 can move vertically at a predetermined position, and be installed to be in contact with the cam part 241 of the driven gear 240. Accordingly, as the cam part 241 rotates, the push rod 251 moves in the vertical direction. In other words, the push rod 251 reciprocates vertically by the rotation of the cam part 241.

Therefore, the ultrasound transducer holder 253 coupled to the push rod 251, the ultrasound transducer 213 coupled to the ultrasound transducer holder 253, and the ultrasound focal point irradiated by the ultrasound transducer 213 can also move vertically or reciprocate vertically.

According to an embodiment of the present invention, the driven gear 240 and the ultrasound radiation moving body 250 may have corresponding grooves and protrusions, or protrusions and grooves for the horizontal movement of the ultrasound radiation moving body 250.

Referring to FIG. 5, the driven gear 240 may have a groove 243, and the push rod 251 may have a protrusion 251*a*. The protrusion 251*a* of the push rod 251 can be inserted into the groove 243 of the driven gear 240.

Accordingly, when the driven gear 240 moves horizontally along the second axis X2, the push rod 251 can also move horizontally, and the ultrasound radiation moving body 250 can also move horizontally. Thus, the ultrasound transducer 213 coupled to the ultrasound radiation moving body 250 and the ultrasound focal point irradiated by the ultrasound transducer 213 can also move horizontally.

Meanwhile, unlike illustrated in FIG. 5, the driven gear 240 may have a protrusion, and the push rod 251 of the ultrasound radiation moving body 250 may have a groove.

According to an embodiment of the present invention, the ultrasound focal point moving cartridge 200 is installed not to be moved vertically, and may further include a carriage 270 which guides the horizontal movement and the vertical movement of the ultrasound radiation moving body 250.

Referring to FIGS. 3 to 5, horizontal guide pins 221*b* can be installed in the horizontal direction between the two wall parts 221*a* of the cartridge bracket 221. The horizontal direction can be horizontal to the first axis X1 or the second axis X2. Additionally, the carriage 270 can have horizontal guide holes 271 in the horizontal direction. The horizontal guide pins 221*b* pass through the horizontal guide holes 271 of the carriage 270, thereby guiding the horizontal movement of the carriage 270. Thus, the horizontal movement of the ultrasound radiation moving body 250 moving with the carriage 270 can also be guided.

In one aspect, the carriage 270 may have vertical guide holes 273 in the vertical direction. Furthermore, the ultrasound transducer holder 253 of the ultrasound radiation moving body 250 may have vertical guide pins 253*a*. The vertical guide pins 253*a* of the ultrasound transducer holder 253 are inserted into the vertical guide holes 273 of the carriage 270, thereby guiding the vertical movement of the ultrasound transducer holder 253 and the vertical movement of the ultrasound radiation moving body 250.

Meanwhile, for vertical movement of the ultrasound focal point, only the ultrasound radiation moving body 250 may move vertically, and the carriage 270 can be installed not to be moved vertically. Since the relatively large and heavy carriage 270 is not moved vertically, vibration and noise can be reduced, and the durability of the device can be improved. Particularly in the present invention, the vertical movement involves the very short reciprocating movement, so may generate significant vibration and noise. Accordingly, the vertical movement of the carriage 270 may be restricted, thereby effectively preventing the occurrence of the vibrations and noise, and improving the durability of the device.

According to an embodiment of the present invention, between the ultrasound radiation moving body 250 and the carriage 270, an elastic means that supplies elastic force to ensure that the ultrasound radiation moving body 250 is pressed against the cam part 241 of the driven gear 240 can be provided.

Referring to FIGS. 4 and 5, an elastic means can be provided between the push rod 251 and the carriage 270, and the elastic means may be a coil spring 257. The coil spring 257 provides elastic force to push the push rod 251 so that the push rod 251 is pressed against the cam part 241.

Meanwhile, unlike illustrated in FIGS. 4 and 5, the elastic means can be provided between the ultrasound transducer holder 253 and the carriage 270. In a such case, the elastic means pulls the ultrasound transducer holder 253 toward the carriage 270, thereby causing the push rod 251 to be pressed against the cam part 241.

By being pressed against the cam part 241, the ultrasound radiation moving body 250 can smoothly move vertically due to the rotation of the cam part 241.

Hereinafter, referring to FIG. 7, the horizontal movement of the ultrasound focal point will be described.

Figure 7:
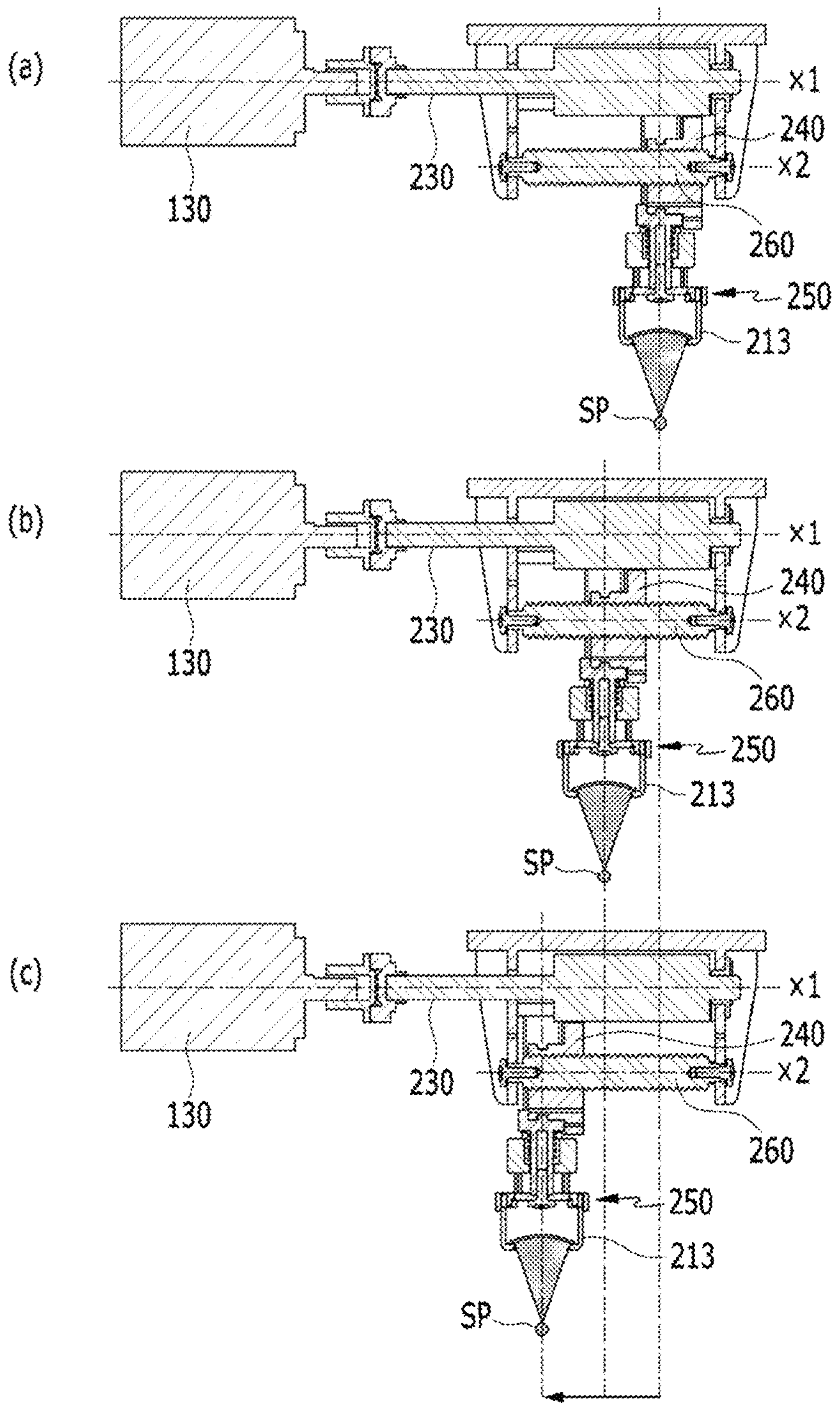
FIG. 7 is a view illustrating the horizontal movement of the ultrasound focal point.

FIG. 7 is a view illustrating the horizontal movement of the ultrasound focal point, showing that the ultrasound focal point moves horizontally in order of FIGS. 7 (*a*), 7 (*b*) and 7 (*c*). In the drawing, the ultrasound focal point moves from right to left.

Referring to FIG. 7, the driving force of the motor 130 is transmitted to the drive gear 230, and the drive gear 230 can rotate in one direction around the first hypothetical axis X1 upon receiving the driving force.

When the drive gear 230 rotates, the driven gear 240 can rotate in the opposite direction around the second hypothetical axis X2 due to the engagement of the gears. The second axis X2 may be a horizontal axis horizontal to the first axis X1. The opposite direction may be a reverse direction to the one direction.

The driven gear 240 rotates and simultaneously moves horizontally along the lead screw 260. The lead screw 260 is installed along the second axis X2 and is fixed in place not to be moved.

When the driven gear 240 moves horizontally, the ultrasound radiation moving body 250 can also move horizontally. Accordingly, the ultrasound transducer 213 also moves horizontally along with the ultrasound radiation moving body 250, and thus, the ultrasound focal point SP irradiated by the ultrasound transducer 213 also moves horizontally.

Meanwhile, when the driven gear 240 reaches the left or right end due to the horizontal movement, a sensor (not shown) may be installed to detect the position of the driven gear. The sensor may be a photo sensor, a magnetic sensor, or a hall sensor, which senses the position of the driven gear 240 and/or the ultrasound radiation moving body 250. If the sensor detects that the driven gear 240 or the ultrasound radiation moving body 250 has reached a predetermined position at the left or right end, the motor 130 can rotate in the reverse direction to the rotational direction. Accordingly, the driven gear 240 can move horizontally towards the opposite side of the left or right end, namely, to the right or left.

Hereinafter, the vertical movement of the ultrasound focal point will be described with reference to FIG. 8.

Figure 8:
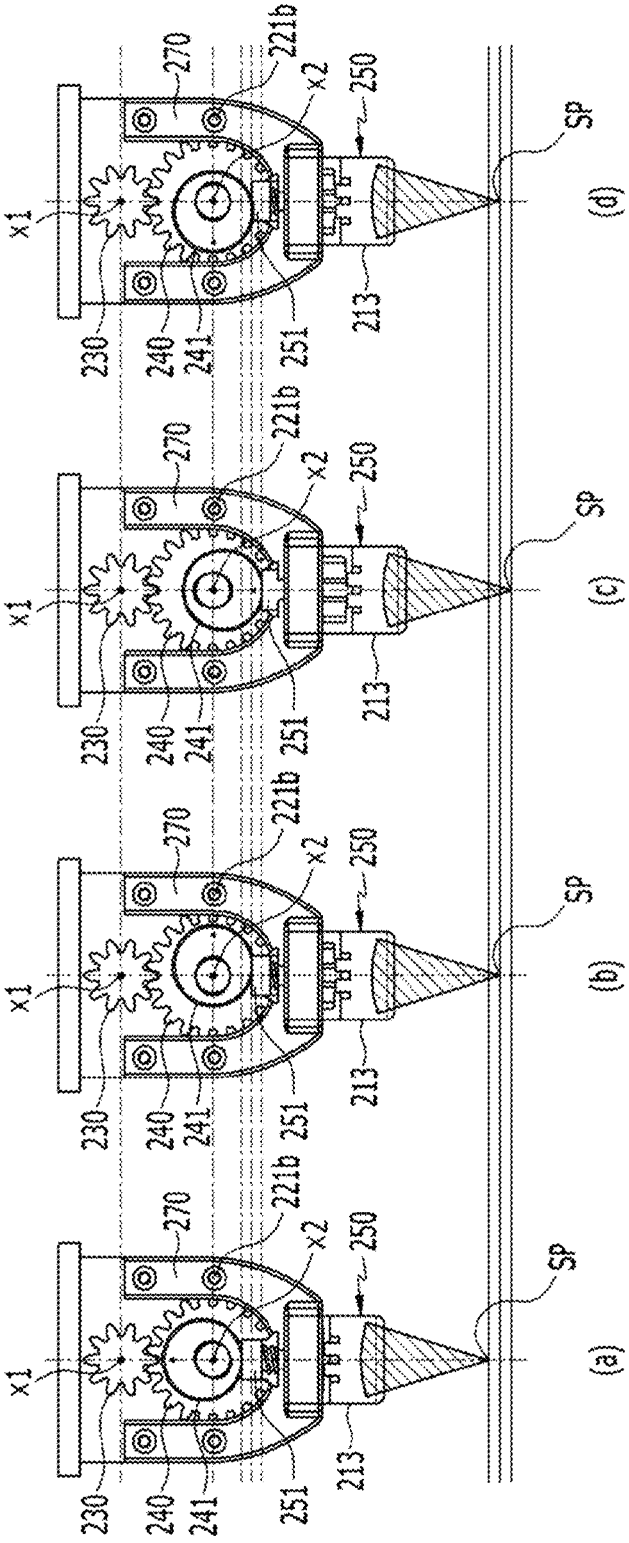
FIG. 8 is a view illustrating the vertical movement of the ultrasound focal point.

FIG. 8 is a view illustrating the vertical movement of the ultrasound focal point. FIG. 8 shows that the ultrasound focal point moves horizontally as the driven gear 240 rotates in the clockwise direction in order of (a), (b) and (c) in FIG. 8.

Referring to FIG. 8, the driving force of the motor 130 is transmitted to drive gear 230, and the drive gear 230 rotates in one direction around the first hypothetical axis X1 upon receiving this driving force.

When the drive gear 230 rotates, the driven gear 240 can rotate in the opposite direction around the second hypothetical axis X2 due to the engagement of the gears. The second axis X2 may be a horizontal axis horizontal to the first axis X1. The opposite direction may be a reverse direction to the one direction. When the driven gear 240 rotates, the cam part 241, which is eccentric to the second axis X2, also rotates.

Accordingly, the push rod 251, which is in contact with the cam part 241 and is mounted to move vertically at a predetermined position, also moves vertically. When the driven gear 240 rotates in the clockwise direction in order of FIGS. 8 (*a*), 8 (*b*), 8 (*c*) and 8 (*d*), the cam part 241 also rotates in the clockwise direction. So, the push rod 251 moves vertically in order of the highest point, the midpoint, the lowest point, and the midpoint. Therefore, the ultrasound transducer 213 and the ultrasound focal point SP irradiated by the ultrasound transducer 213, which are mounted to move vertically with the push rod 251, also move vertically in the same order.

Meanwhile, as described above, the carriage 270 that guides the vertical movement of the ultrasound radiation moving body 250 can be installed not to be moved vertically. Referring to FIG. 8, the carriage 270 can move horizontally along the horizontal guide pins 221*b* but is installed not to be moved vertically. Since the carriage 270, which has a relatively large volume and mass, does not move vertically, vibration and noise can be reduced. Particularly in the present invention, the vertical movement involves the very short reciprocating movement, so may generate significant vibration and noise. Accordingly, the vertical movement of the carriage 270 may be restricted, thereby effectively preventing the occurrence of the vibrations and noise, and improving the durability of the device.

As described above, the foregoing embodiments and advantages are merely exemplary and are not to be construed as limiting the present invention. The present teaching can be readily applied to other types of apparatuses. The description of the foregoing embodiment is intended to be illustrative, and not to limit the scope of the claims. Many alternatives, modifications, and variations will be apparent to those skilled in the art.

The invention claimed is:

1. An ultrasound focal point moving cartridge comprising:
- a drive gear rotatably installed around a first axis;
- a driven gear configured to rotate around a second axis parallel to the first axis and move horizontally along the second axis by rotation power received from the drive gear; and
- an ultrasound irradiation moving body which is horizontally moved with the driven gear and vertically moved in a direction perpendicular to the first axis or the second axis.

2. The ultrasound focal point moving cartridge according to claim 1, wherein the driven gear moves along a lead screw which is fixedly installed along the second axis.

3. The ultrasound focal point moving cartridge according to claim 1, wherein the driven gear includes a cam part eccentric to the second axis, and
- wherein the ultrasound radiation moving body includes a push rod which is in contact with the cam part.

4. The ultrasound focal point moving cartridge according to claim 1, wherein the driven gear and the ultrasound radiation moving body respectively include a groove and a protrusion corresponding to each other, or a protrusion and a groove, for the horizontal movement of the ultrasound radiation moving body.

5. The ultrasound focal point moving cartridge according to claim 1, further comprising a carriage,
- wherein the carriage is installed not to be moved vertically, and guides the horizontal movement and the vertical movement of the ultrasound radiation moving body.

6. The ultrasound focal point moving cartridge according to claim 5, wherein between the ultrasound radiation moving body and the carriage, an elastic means which supplies elastic force so that the ultrasound radiation moving body is pressed against a cam part of the driven gear is provided.

7. An ultrasound treatment device including the ultrasound focal point moving cartridge according to claim 1.

* * * * *